(12) United States Patent
Bauer et al.

(10) Patent No.: US 7,129,666 B2
(45) Date of Patent: Oct. 31, 2006

(54) MOTORIZED ADJUSTABLE X-RAY APPARATUS

(75) Inventors: Jochen Bauer, München (DE); Wendelin Feiten, Neubiberg (DE); Manfred Rattner, Grossenseebach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/965,354

(22) Filed: Oct. 14, 2004

(65) Prior Publication Data

US 2005/0151498 A1 Jul. 14, 2005

(30) Foreign Application Priority Data

Oct. 14, 2003 (DE) ................. 103 47 740

(51) Int. Cl.
*G05B 19/33* (2006.01)

(52) U.S. Cl. ............. 318/575; 318/560; 318/567; 318/568.11; 318/569; 318/574; 318/626

(58) Field of Classification Search ........... 318/575, 318/560, 567, 568.11, 569, 574, 626; 378/198; 2/196

See application file for complete search history.

(56) References Cited

U.S. PATENT DOCUMENTS

2004/0042587 A1* 3/2004 Deshpande ............. 378/198

FOREIGN PATENT DOCUMENTS

| DE | 42 37 013 | 5/1994 |
|---|---|---|
| DE | 197 01 346 | 7/1998 |
| DE | 101 11 800 | 10/2002 |

* cited by examiner

*Primary Examiner*—Karen Masih
(74) *Attorney, Agent, or Firm*—Schiff Hardin LLP

(57) ABSTRACT

An x-ray apparatus has a servo-supported C-arm that is movable with two degrees of freedom in a movement space by means of a drive device. The servo support of the C-arm deviates at a stop point within the movement space from the servo support in the surrounding movement space.

11 Claims, 3 Drawing Sheets

MOTORIZED ADJUSTABLE X-RAY APPARATUS

BACKGROUND OF THE INVENTION

1. Field of the Invention

The invention concerns an x-ray apparatus with a servo-controlled adjustable C-arm exhibiting two degrees of freedom.

2. Description of the Prior Art

An x-ray apparatus of the above general type is known, for example, from German OS 42 37 013.

Known from German OS 197 10346 is a medical system with a C-arm in which the C-arm is mounted such that it is adjustable on a supporting frame of an apparatus cart. The apparatus cart can be moved on rails, with items known as stoppers are applied in or on the rails.

A medical-related apparatus that can be moved on wheels is known from German OS 101 11 800. The apparatus is equipped with an electromechanical holding brake (parking brake) that is integrated into an electromotor of an electrical direct drive.

The C-arm of an x-ray apparatus, in particular for medical applications, typically exhibits a heavy weight that is not symmetrically distributed around the movement axes. Compensation weights or a motorized support, i.e. a servo support, can be provided to ease adjustability of the C-arm. In the x-ray apparatus known from German OS 42 37 013, an operating force is detected in order to derive and produce an acceleration of the x-ray apparatus. The operator should hereby receive the impression of moving an x-ray apparatus with significantly a smaller mass or moment of inertia. Servo-aided adjustment, however, frequently makes an exact positioning more difficult.

SUMMARY OF THE INVENTION

An object of the present invention is to provide an x-ray apparatus, with a servo-aided C-arm adjustable in two degrees of freedom, which enables a particularly comfortable and timesaving positioning of the C-arm.

This object is inventively achieved by an x-ray apparatus having a drive device by means of which a C-arm is movable with the aid of servos in a movement space exhibiting two degrees of freedom. At least one stop point, at which the servo support of the C-arm deviates from the servo support in the surrounding movement space is located (present) within the movement space. The stop point preferably is freely selectable as well as being able to be overridden (rescinded) within the entire movement space of the C-arm. Based on the control-dependent realization of the stop point, this is also designated as an electronic locking position ("soft notch"). The establishment of a stop point occurs, for example, by moving the C-arm into a specific position and this position is designated as a stop point, such as by a button press on an operating unit. Alternatively, the coordinates of a stop point can be entered, for example, via a control unit. The servo support of the C-arm at the stop point and in the immediate proximity of the stop point preferably is reduced in comparison to the rest of the servo support of the C-arm. Upon the C-arm nearing the stop point, the user receives the impression that the C-arm is braked at that location. Locating of the stop point as a definite position of the C-arm is hereby significantly eased in comparison with a motorized adjustment of the C-arm with spatially independent servo support. Beyond the reduction of the servo support, at the stop point a braking effect on the C-arm preferably occurs which gives an operator the impression of a distinct engaging event.

The stop point is surrounded by a stop region within which a force pulling the C-arm in the direction of the stop point is exerted by the drive device on the C-arm nearing the stop point. The C-arm is thus "captured" at the stop point by means of the drive device. Fine adjustment of the C-arm at the stop point by the operator is thus not needed.

For safety reasons, the x-ray apparatus preferably has a deadman's switch (release), the continuous operation of which is a requirement for the adjustment of the C-arm. This is also true insofar as the C-arm is drawn into the stop region toward the stop point. A completely independent movement of the C-arm thus is impossible. The operator retains control by means of the deadman's switch of any movement state of the C-arm, meaning the C-arm is directed by the operator in every case.

The servo drive and/or the braking of the C-arm in the region of the stop point can be described by a stopping characteristic curve (which may be composed of straight lines) that preferably exhibits adjustable parameters. A data storage unit, for example integrated into a control unit of the x-ray apparatus, can be provided for storage of these parameters, as well as for the storage of the coordinates of the stop point. Adjustable parameters of the stopping characteristic curve are in particular a retention force with which the C-arm is held at the stop point as well as a maximum attractive force with which the C-arm is drawn in the direction toward the stop point.

The stop point preferably is activated dependent on the movement speed of the C-arm. If the movement speed exceeds an adjustable threshold, no activation of the stop point ensues since in this case it is assumed that the operator does not intend to position the C-arm at the stop point. A further adjustable parameter preferably is an entering angle at which the C-arm, starting from the movement track on which it is directed by the operator, is drawn in the direction of the stop point.

An advantage of the invention is that the number of the stop points in the movement space of the C-arm is not limited. An arbitrary portion of the stop points can be activated or deactivated by the operator at any time.

DESCRIPTION OF THE PREFERRED EMBODIMENTS

Figure 1:
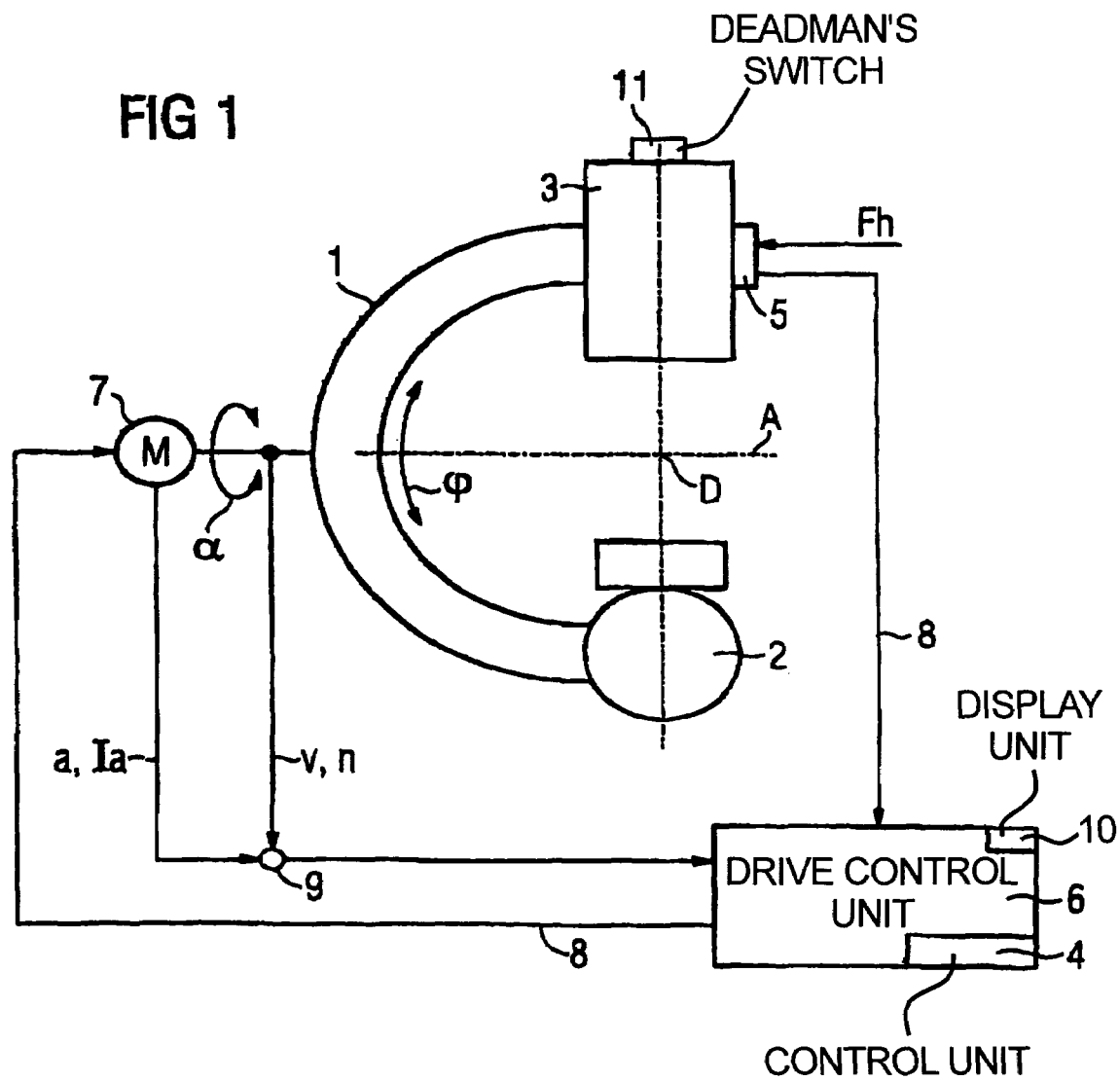
FIG. 1 schematically illustrates an x-ray apparatus with a servo-aided adjustable C-arm exhibiting two degrees of freedom operable in accordance with the invention.

Parts and parameters corresponding to each other are provided with the same reference characters in all figures.

An x-ray apparatus shown schematically in FIG. 1 has a C-arm 1 on which an x-ray radiator 2 is mounted on one end and an image acquisition system 3 is mounted on the opposite end. Two degrees of freedom of the C-arm 1 exist by adjustment of an angulation angle $\alpha$ and an orbital angle $\phi$. A rotation point is designated D, a rotation axis is designated A. A force transducer 5 detects and measures a manual force Fh of an operator and supplies an electrical signal corresponding thereto to a control unit 6 via a line 8. The force transducer 5 preferably is fashioned to separately detect a number of directional components of the force Fh. A single force transducer 5 thus is sufficient to adjust the C-arm both in the direction of the angulation angle α and in the direction of the orbital angle φ. Movement of the C-arm in the orbital and/or angular direction requires activation of a deadman's switch 11 which is likewise linked (in a manner not shown in detail) with the control unit 6. Furthermore, the control unit 6 has a data storage unit 4 as well as a display unit 10, for example in the form of a text display, a light display or an acoustic indication.

The control unit 6, together with an electromotor 7 controlled thereby, forms a drive device. Signals regarding acceleration a of the x-ray apparatus 1, 2, 3, an armature current Ia of the electromotor 7, a movement speed v of the x-ray apparatus 1, 2, 3 as well as the rotation speed n of the electromotor 7 are supplied to the control unit 6 via a comparator 9. The stop function of the drive device 6, 7 is subsequently explained in detail using FIGS. 2 and 3.

Figure 2:
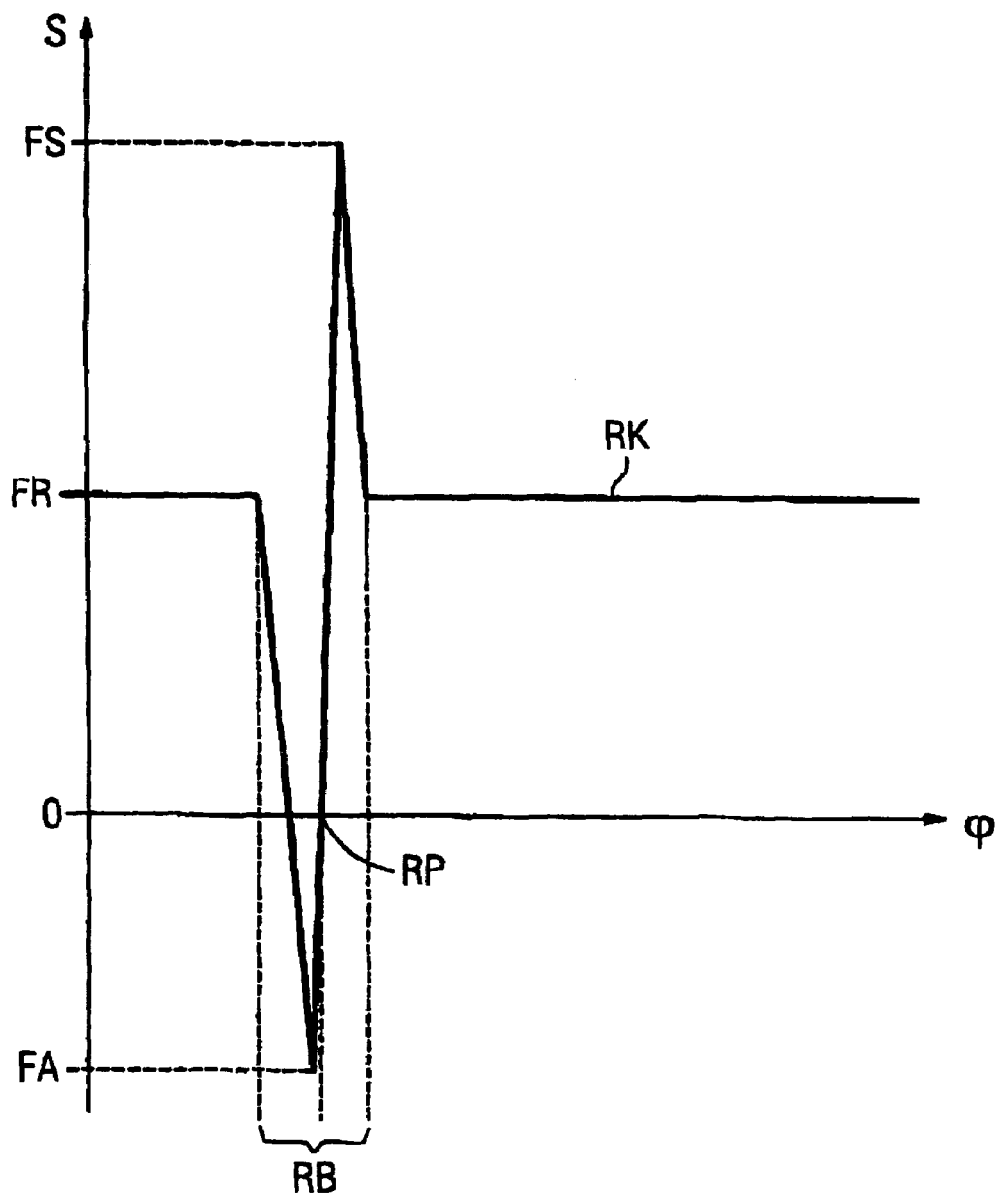
FIG. 2 shows a stopping characteristic curve of the x-ray apparatus according to FIG. 1.

A servo-support S, generated with the aid of the electromotor 7 for the adjustment of the C-arm 1, is shown dependent on the orbital angle φ in a schematized diagram according to FIG. 2. The dependency of the servo support 5 on the angulation angle α or on an arbitrary movement path of the C-arm 1 with variable angles α,φ could also be used. Given adjustment of the C-arm 1 with constant angular speed, a force FR, which can be interpreted by the operator as a friction force is effected on the C-arm 1. The force FR is such that the C-arm 1 can be relatively easily adjusted in comparison to its heavy weight.

A deviation from the otherwise uniform servo support S of the C-arm 1 that indicates the force acting on the C-arm 1 occurs at a stop point RP and in a stop region RB encompassing the stop point RP. Insofar as the stop curve RK shown in FIG. 2 runs in the positive region, a braking force to be overcome by the operator acts on the C-arm 1. In contrast to this, given progression of the stop curve RK into the negative region the C-arm 1 approaching the stop point RP is drawn to the stop point RP with a resulting force. A property typically encountered with a mechanical stoppage is therewith reproduced in a control-dependent manner by the control unit 4. The stop point RP therefore is also designated as an electronic locking position or "soft notch". In order to move the C-arm 1 further from the stop point RP, a force threshold FS must first be overcome, which is adjustable just as a maximum attracting force FA that previously drew the C-arm 1 to the stop point RP. Positioning of the C-arm 1 at the stop point RP stored in the data storage 4 is indicated by the display unit 10. A new stop point RP can be defined, for example, by moving the C-arm 1 into the corresponding position and triggering a storage function via which the corresponding values of the orbital angle φ as well as the angulation angle α are stored. It is preferably additionally possible to provide a stop function in which only one of the angles φ,α has a determined value. A stop line of the C-arm 1 can be established with this. Any arbitrary stop line in space, meaning a stop line in which neither the orbital angle φ nor the angulation angle α is constant, can be established in an analogous manner.

Figure 3:
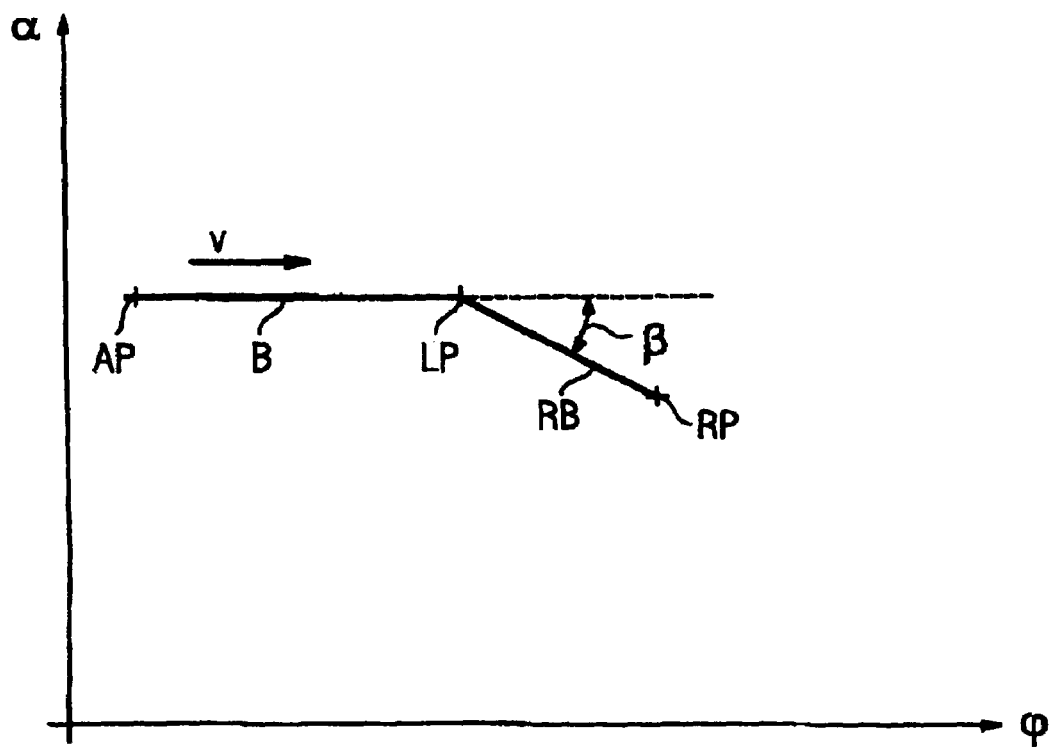
FIG. 3 shows, schematically in a diagram, a movement path of the C-arm of the x-ray apparatus according to FIG. 1.

In FIG. 3, an example of a movement path of the C-arm 1 is illustrated in the movement space exhibiting two degrees of freedom and given by the angulation angle α and the orbital angle φ. Starting from a starting point AP, the C-arm 1 is first directed along a movement path B with constant movement speed v. This would pass a stop point RP in the movement space. Insofar as the movement speed v does not exceed an adjustable speed threshold, in the stop region RP an active attraction of the C-arm 1 to the stop point RP ensues corresponding to the diagram according to FIG. 2. The C-arm 1 is thereby deflected from its original movement path B at a deflection point LP. The angle between a tangent of the movement path B at the deflection point LP and a straight line through the deflection point LP and the stop point RP is designated as an entering angle β. The adjustment of the C-arm 1 within the stop region RP does not necessarily ensue in the shown linear manner. The entering angle β is adjustable. While a particularly gentle approach of the stop point RP with low acceleration is enabled with a low entering angles β, a particularly notable engagement of the drive device 6, 7, and therewith an easy locating of the stop point RP, is achieved with larger entering angles β. Various stop points RP within the movement space of the C-arm 1 are realized in a control-dependent manner as needed for easier differentiability, with different parameters that are selected as explained above using FIGS. 2 and 3. Each stop point RP can be arbitrarily activated, deactivated or shifted.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus comprising:
   a servo-supported C-arm;
   a drive device connected to said C-arm that allows servo-supported movement of said C-arm in two degrees of freedom in a movement space in response to a manual force applied to said region of said movement space near a C-arm; and
   said drive device automatically sensing when said C-arm enters a predetermined stop point within said movement space and deviating said servo support of said C-arm, in said region, from the servo-support of the C-arm outside of said region of the movement space, by exerting an attractive force on said C-arm in a direction toward said stop point in said region near said stop point.

2. An x-ray apparatus as claimed in claim 1 comprising a deadman's switch connected to said drive device allowing movement of said C-arm by said drive device only as long as said deadman's switch is activated.

3. An x-ray apparatus as claimed in claim 1 comprising a data storage unit accessible by said drive device in which a location of said stop point is stored.

4. An x-ray apparatus as claimed in claim 1 wherein said data storage unit contains a characteristic stopping curve for said C-arm with respect to said stop point.

5. An x-ray apparatus as claimed in claim 4 wherein said characteristic stopping curve exhibits a force threshold that determines a retention force of said c-arm at said stop point.

6. An x-ray apparatus as claimed in claim 5 comprising an input unit allowing adjustment of said force threshold of said characteristic stopping curve.

7. An x-ray apparatus as claimed in claim 4 wherein said characteristic stopping curve has a maximum attracting force that can be exerted on said C-arm in said stop region by said drive device.

8. An x-ray apparatus as claimed in claim 7 comprising an input device allowing adjustment of said maximum attracting force.

9. An x-ray apparatus as claimed in claim 1 wherein said drive device detects an entering angle at which said C-arm, in a movement path in said movement space, is drawn in the direction of said stop point, and wherein said drive device alters acceleration of said C-arm relative to said stop point dependent on said entering angle.

10. An x-ray apparatus as claimed in claim 9 comprising an input unit allowing adjustment of said entering angle.

11. An x-ray apparatus as claimed in claim 1 wherein said drive device overrides the deviation of the servo-support of the C-arm at said stop point dependent on a movement speed of said C-arm in said movement space.

* * * * *